United States Patent
Garrigue et al.

(10) Patent No.: US 12,403,297 B2
(45) Date of Patent: Sep. 2, 2025

(54) INTRAVENTRICULAR HEART PUMP WITH NARROWED HEAD

(71) Applicant: FINEHEART, Pessac (FR)

(72) Inventors: Stéphane Garrigue, Begles (FR); Arnaud Mascarell, Montbazon (FR)

(73) Assignee: FINEHEART, Pessac (FR)

( * ) Notice: Subject to any disclaimer, the term of this patent is extended or adjusted under 35 U.S.C. 154(b) by 0 days.

(21) Appl. No.: 18/722,272

(22) PCT Filed: Dec. 1, 2022

(86) PCT No.: PCT/EP2022/084129
§ 371 (c)(1),
(2) Date: Jun. 20, 2024

(87) PCT Pub. No.: WO2023/117368
PCT Pub. Date: Jun. 29, 2023

(65) Prior Publication Data
US 2025/0082921 A1    Mar. 13, 2025

(30) Foreign Application Priority Data

Dec. 21, 2021   (FR) ...................................... 2114112

(51) Int. Cl.
*A61N 1/362*      (2006.01)
*A61M 60/178*     (2021.01)
(Continued)

(52) U.S. Cl.
CPC ........ *A61M 60/178* (2021.01); *A61M 60/216* (2021.01); *A61M 60/422* (2021.01); *A61M 60/538* (2021.01)

(58) Field of Classification Search
CPC .. A61M 2205/3365; A61M 2205/8206; A61M 2206/20; A61M 60/148;
(Continued)

(56) References Cited

U.S. PATENT DOCUMENTS

| 5,147,388 A | 9/1992 | Yamazaki |
| 5,324,177 A | 6/1994 | Golding et al. |
(Continued)

FOREIGN PATENT DOCUMENTS

| CA | 2472088 A1 | 9/2003 |
| CA | 2517236 A1 | 11/2004 |
(Continued)

OTHER PUBLICATIONS

International Preliminary Report on Patentability (IPRP/IPER) received for PCT/EP2022/084129, mailed Mar. 13, 2024. (Official PCT-WIPO Translation).

(Continued)

*Primary Examiner* — Jon Eric C Morales
(74) *Attorney, Agent, or Firm* — Greer, Burns & Crain, Ltd

(57) ABSTRACT

A heart pump intended to be positioned in a ventricle of a heart and to generate an induced flow of fluid in the direction of the sigmoid valves; the pump includes a fixed casing provided with a top part forming a propulsion chamber for propelling the fluid towards the top end, and a bottom part, at least one side opening between the top part and the bottom part and forming a chamber for fluid inlet from the outside towards the propulsion chamber, and a power unit arranged inside the casing to drive the fluid from the side opening right up to the outlet of the propulsion chamber. The propulsion chamber includes an upper body and an outlet head; the outlet head having a narrowed external cross section with respect to an external cross section of the upper body.

13 Claims, 3 Drawing Sheets

(51) Int. Cl.
*A61M 60/216* (2021.01)
*A61M 60/422* (2021.01)
*A61M 60/523* (2021.01)
*A61M 60/538* (2021.01)
*A61M 60/873* (2021.01)

(58) Field of Classification Search
CPC .. A61M 60/165; A61M 60/17; A61M 60/221; A61M 60/232; A61M 60/237; A61M 60/416; A61M 60/422; A61M 60/515; A61M 60/523; A61M 60/804; A61M 60/806; A61M 60/812; A61M 60/827
See application file for complete search history.

(56) References Cited

U.S. PATENT DOCUMENTS

| | | |
|---|---|---|
| 6,234,772 B1 | 5/2001 | Wampler et al. |
| 10,954,954 B2 | 3/2021 | Haddadi et al. |
| 11,020,584 B2 | 6/2021 | Siess et al. |
| 11,376,414 B2 | 7/2022 | Haddadi et al. |
| 2003/0124007 A1 | 7/2003 | Schima et al. |
| 2018/0243489 A1* | 8/2018 | Haddadi ............ A61M 60/523 |
| 2018/0311421 A1 | 11/2018 | Tuseth et al. |
| 2021/0260359 A1 | 8/2021 | Bonde |

FOREIGN PATENT DOCUMENTS

| | | |
|---|---|---|
| EP | 2734251 B1 | 8/2016 |
| WO | 2018197306 A1 | 11/2018 |

OTHER PUBLICATIONS

International Search Report and Written Opinion received for PCT/EP2022/084129, mailed Mar. 15, 2023. (Certification of Translation included).

French Search Report received for Application No. 2114112, dated Aug. 5, 2022.

* cited by examiner

INTRAVENTRICULAR HEART PUMP WITH NARROWED HEAD

BACKGROUND

The present invention relates to a pump, in particular an axial pump, intended to be immersed in a fluid.

The present invention relates more particularly, but not exclusively, to a pump for ventricular assistance. It concerns, for example, a pump supplied by a battery and intended to be inserted into a human body to assist the circulation of the blood.

Heart failure (HF), progressive inability of the heart to supply a blood flow necessary for the metabolic needs of an individual in daily life, is the second cause of mortality in Western countries. The treatment for heart failure, which consists of increasing the blood flow suitably for the needs of the patient, is making progress but still remains inadequate.

An intraventricular heart pump is intended to be inserted into a systemic ventricle of the heart of a patient. Not all hearts have identical dimensions. It could be necessary to design several pumps of different sizes.

SUMMARY

The purpose of the present invention is to avoid such designs by proposing a new pump suitable for being compatible with many sizes of heart.

Another purpose of the invention is a pump that is efficient regardless of the state of the heart, dilated or not.

At least one of the objectives is achieved with a heart pump intended to be positioned partially or entirely in a ventricle of a heart and to generate an induced flow of fluid in the direction of the sigmoid valves of the aorta; this pump comprising:
- a fixed casing provided with a top part, when the heart pump is positioned vertically, forming a propulsion chamber for propelling the fluid towards the top end, and a bottom part attached in a fixed manner to the top part,
- at least one side opening between the top part and the bottom part and forming a chamber for fluid inlet from the outside towards the propulsion chamber,
- a power unit arranged inside the casing to drive the fluid from the side opening right up to the outlet of the propulsion chamber.

According to the invention, the propulsion chamber comprises an upper body and an outlet head; the outlet head having a narrowed external cross section with respect to an external cross section of the upper body; the outlet head having an external cross section the diameter, or largest distance, of which is comprised between 14 and 16 mm.

By "cross section" is meant the area of the surface seen according to a section perpendicular to the axis of propulsion of the fluid. By "external cross section" is meant a cross section the contour of which fits closely to the outer contour of the propulsion chamber, as opposed to an internal cross section which would relate to the internal volume in which the fluid circulates.

The pump according to the present invention has the advantage of having a narrowed head the dimension of which is suitable for efficiently propelling the fluid towards the sigmoid valves at the inlet of the aorta. The range of 14 to 16 mm makes it possible to have an outlet head that is suitable regardless of the state of the heart. In fact, whether the heart is dilated or not, whether it is a child's heart or an adult's heart i.e. a small heart or a large heart, the range defined by the present invention makes it possible to efficiently position the pump close to the aorta without coming into contact. By "close" is meant a distance that is sufficient for the propelled flow of fluid to be powerful enough to separate the sigmoid valves and for the fluid to enter the aorta. This distance depends on the power of the pump.

One and the same heart can have different dimensions. For example, a dilated heart has a volume that is significantly greater than the volume of the same heart in a non-dilated situation. Remarkably, the dimension of the inlet of the aorta remains identical regardless of the level of dilation of the heart.

The dimension of the head also allows the passage of a natural or spontaneous flow. In the context of heart failure, the heart can still be capable of contracting to expel the fluid towards the aorta, albeit inadequately. The flow created is thus a natural flow while the flow generated by the pump is an induced flow which provides the majority of, or replaces, the natural flow.

To this end, proposing a fixed dimension for the outlet head comprised between 14 mm and 16 mm according to the invention, allows good circulation of the induced and natural flows. This dimension allows a sufficient passage of the natural flow around the head.

According to an advantageous characteristic of the invention, the external cross section of the upper body can have a diameter, or a largest distance, comprised between 17 and 20 mm.

According to an embodiment of the invention, the external cross section of the upper body has a diameter, or a largest distance, equal to 18 mm.

With such an arrangement, the upper body is suitably dimensioned to accommodate means for propelling the fluid towards the outlet head. The upper body is larger than the outlet head.

Advantageously, the outlet head can have a distance along a propulsion axis comprised between 5 and 10 mm. Such a head can for example be in the shape of a right cylinder guiding the flow of fluid towards the outside in the direction of the aorta.

The outlet head can for example include vanes, the set of vanes constituting a straightener capable of increasing the speed and giving the fluid a predefined profile at the outlet.

According to an additional characteristic, the pump according to the invention can comprise a shoulder where the upper body and the outlet head meet, this shoulder having a concave shape. By "concave shape" is meant a shape that is rounded towards the inside so that the natural flow flows along the shoulder without stagnation.

According to an advantageous characteristic of the invention, the propulsion chamber can be in the shape of a right circular cylinder.

According to an advantageous embodiment, the upper body can have an outer shape that is flared from the inlet chamber right up to the outlet head. Preferably, the diameter of the propulsion chamber develops progressively with no shoulder.

The diameter of the head can be less than, greater than or equal to the smallest diameter of the propulsion chamber.

In particular, in addition in to the above, the propulsion chamber can be attached in a fixed manner to the bottom part of the casing by means of linking elements the top part of which is directly connected to the bottom end of the propulsion chamber, the outer surface of the propulsion chamber being flush with the linking elements at the place of connection.

According to the invention, the linking elements can have a general shape that is curved outwards. The curved shape can mean that the linking elements are inscribed along a rounded, globally spherical shape, the diameter of which is greater than the diameter of the bottom end of the propulsion chamber and than the diameter of the top end of the bottom part of the casing.

By way of example, the linking elements can comprise four pillars.

According to an advantageous characteristic of the invention, the pillars can include prolongations right up to the inside of the propulsion chamber; these prolongations serving as inducer vanes to make the flow of the fluid linear in the direction of the top part of the casing.

For example, the pillars can be attached to one another by a lateral band arranged at a distance from the ends of these pillars.

According to an embodiment of the invention, the propulsion chamber can comprise a rotor to propel the fluid towards the outlet head.

Advantageously, the pump can comprise a processing unit configured to control the rotor according to a pulsed mode.

BRIEF DESCRIPTION OF THE DRAWINGS

Other advantages and characteristics of the invention will become apparent on examination of the detailed description of an embodiment which is in no way limitative, and from the attached drawings, in which.

DETAILED DESCRIPTION

The embodiments that will be described hereinafter are in no way limitative; variants of the invention can in particular be implemented comprising only a selection of the characteristics described hereinafter, in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described are intended to be combined together in any combination, if there is no objection thereto from a technical point of view.

In the figures, elements common to several figures retain the same reference.

Figure 1:
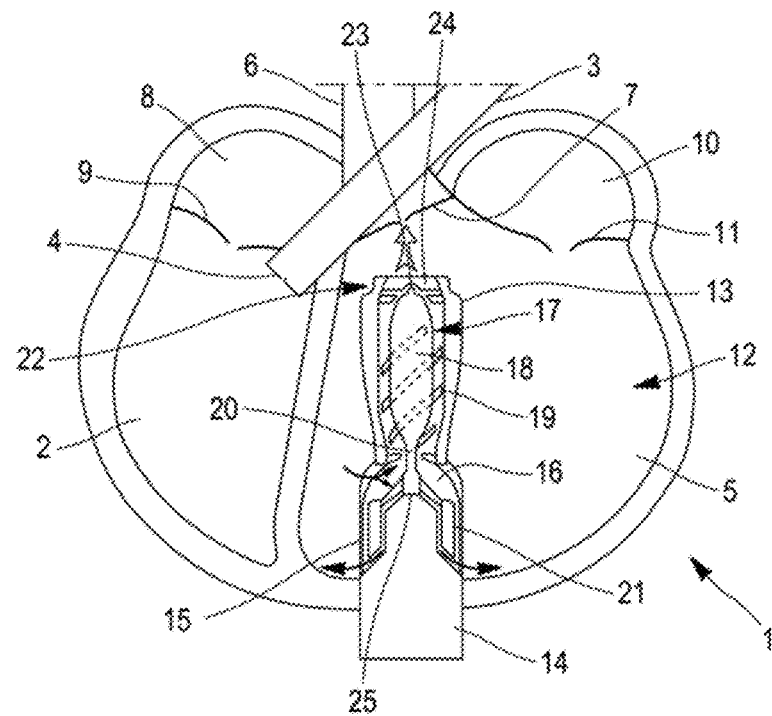
FIG. 1 is a general view of an intraventricular heart pump according to the invention.

FIG. 1 shows an intraventricular heart pump.

The heart as a whole is denoted by the reference 1. The right ventricle 2, which has the function of ejecting the blood towards the pulmonary artery 3 via the sigmoid valves 4, is shown. The left ventricle 5 has the function of carrying out the systemic circulation by ejecting the oxygenated blood towards the aorta 6 via sigmoid valves 7.

The right atrium 8 feeds the right ventricle 2 with blood via the atriopulmonary valves 9. The left atrium 10 feeds the left ventricle 5 with blood via the atriopulmonary valves 11.

The pump as a whole according to the invention is referenced 12. It is fixed at the apex of the left ventricle 5. It can be connected wired or wirelessly to a management unit (not shown) external to the heart. It can be connected to one or more probes or sensors (not shown) for detecting the heart rate or other.

The bottom part of the pump housing the motor can be partially external to the heart, partially within the thickness of the apex or entirely within the heart. In the example in FIG. 1, the bottom part of the pump is partially external to the heart, which can be an advantage for maintenance of the motor in particular.

The pump comprises a casing constituted by a top part 13 rigidly attached to a bottom part 14 by means of linking elements 15. These linking elements can comprise one or more pillars 15 attaching the two parts 13 and 14 while leaving wide passages for the blood.

In the example in FIG. 1, the bottom part 14 constitutes the stator of a motor. The casing, 13, 14 and 15, is intended to remain fixed. Between the top part 13 and the bottom part 14, there is an inlet chamber 16 which is an open space, only obstructed by the linking elements 15. In operation, the pump is intended to draw the blood contained in the ventricle 5 via the inlet chamber 16, convey it through the top part 13 of the casing and eject it by the top outlet towards the valve 7.

In order to draw the blood, the pump comprises an impeller 17 designed on the basis of an oblong body 18 around which is wound one or more helical vanes 19. In rotation, the impeller draws the blood and propels it towards the outlet. This is the main function of the pump. The main flow is therefore that which is pumped by the impeller 17.

The impeller is borne by a transmission shaft 20 which includes at the end opposite the impeller, a bell 21. The assembly of impeller 17, transmission shaft 20 and bell 21 is rigid and suitable for performing rotations. To this end, the bell 21 constitutes the rotor of the motor formed with the fixed stator 14. This motor 14 and 21 is a motor of the brushless type with an external rotor. This is a synchronous machine equipped with an electronic control system (not shown), accessible from outside the heart or not.

The impeller is suitable for performing rotational movements about its axis and relative to the casing 13, 14, which remains fixed. An inlet pivot 25 and an outlet pivot 23 are located within the axis of rotation of the impeller and hold the impeller within its axis when it is in magnetic suspension during the rotational movements. In a variant (not shown) one or both of the two pivot zones can comprise connections with bearings allowing the rotation of the impeller.

The invention is notable in particular for the fact that the top part 13 of the casing comprises an outlet head 22 to propel the blood out of the pump, in the direction of the aorta 6.

Figure 2:
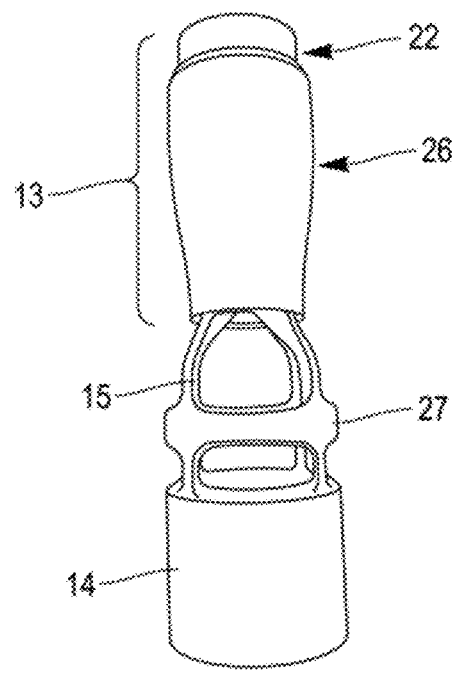
FIG. 2 is a perspective view of a casing of an intraventricular heart pump according to the invention.

FIG. 2 illustrates a perspective view of a pump according to the invention. The bottom part 14, the pillars 15 and the top part 13 can be seen. The latter comprises an upper body 26 and the outlet head 22. The upper body 26 has a flared shape, the dimensions increasing from the pillars 15 right up to the outlet head 22. The upper body 26 finishes with a shoulder reducing its diameter to connect the outlet head which has a diameter less than the diameter of the top part of the upper body (when the pump is arranged vertically, the bottom part being downwards).

A lateral band 27 is also provided attaching the pillars to one another so as to support the pillars of the inlet chamber, while leaving openings for the inlet of the blood and the evacuation of return blood between the bell 21 and the fixed bottom part 14.

Figure 3:
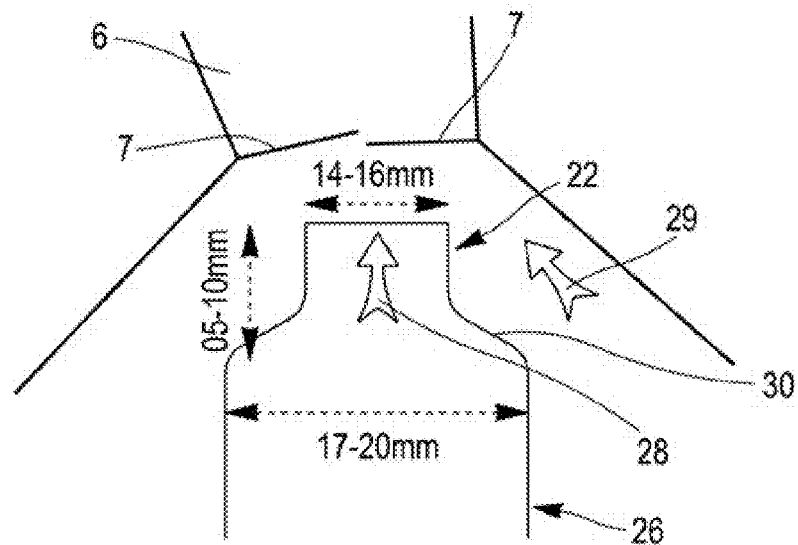
FIG. 3 is a simplified diagrammatic view illustrating the dimensions of a narrowed head according to the invention.

FIG. 3 is a diagrammatic view illustrating some dimensions of the outlet head and of the upper body.

The present invention requires the diameter of the outlet head to be fixed between 14 and 16 mm. This range of values makes it possible for both an induced flow 28 originating from the pump and a spontaneous or natural flow 29 originating from the natural contraction of the heart to coexist. In fact, this dimensioning is compatible with any dimension of heart and regardless of the state of the heart, i.e. dilated or not. The narrowing of the head allows an efficient positioning of the pump, close to the aorta without however blocking the passage of the spontaneous flow. The diameter of the head is large enough to be able to generate a flow capable of reaching the aorta.

Preferably, the height of the outlet head is comprised between 5 and 10 mm. A bend 30 makes it possible to create the connection between the outlet head 22 having a reduced diameter and the upper body 26 having a diameter greater than the diameter of the outlet head. The upper body has on its top part a diameter comprised between 17 and 20 mm. In particular, when the diameter of the upper body is greater than 17 mm, it is intended that the diameter of the outlet head can reach 17 mm.

Figure 4:
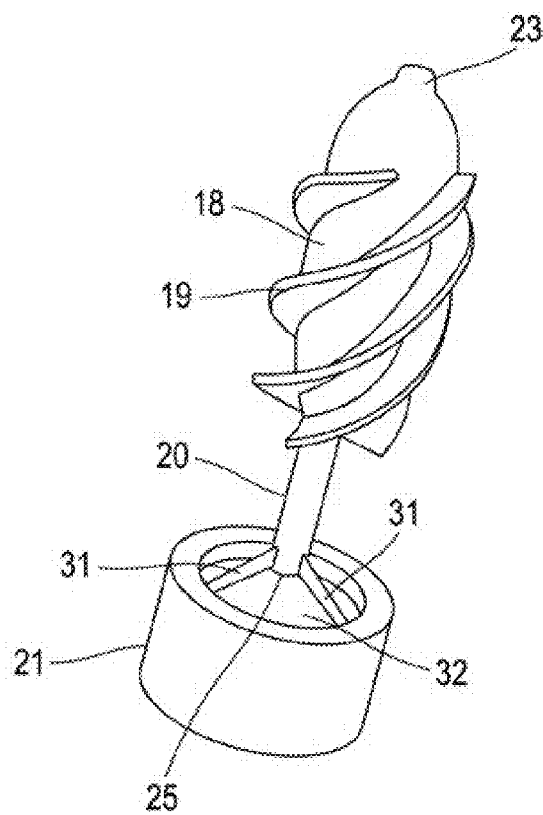
FIG. 4 is a diagrammatic view of an impeller having helical vanes on the outside of the rotor according to the invention.

FIG. 4 shows the impeller 17 in a little more detail, attached to the transmission shaft 20 and to the bell 21. The outlet pivot 23, in the shape of a hemisphere, is located at the apex of the impeller and within the axis of rotation. The helical vanes 19 surround the body 18 from the foot until covering approximately three-quarters of the body 18. The apex of the impeller is devoid of vanes.

The transmission shaft 20 is solidly connected to side vanes 31, two of which are visible and a third hidden. There are three side vanes, but there may be only one, two or more than three. In any event, the side vanes 31 must leave openings 32 so that the fluid can enter the interior of the bell 21. In the example shown, the inlet pivot 25 is located above the bell 21, but other embodiments can be envisaged where the inlet pivot is arranged in the interior of the bell 21.

Figure 5:
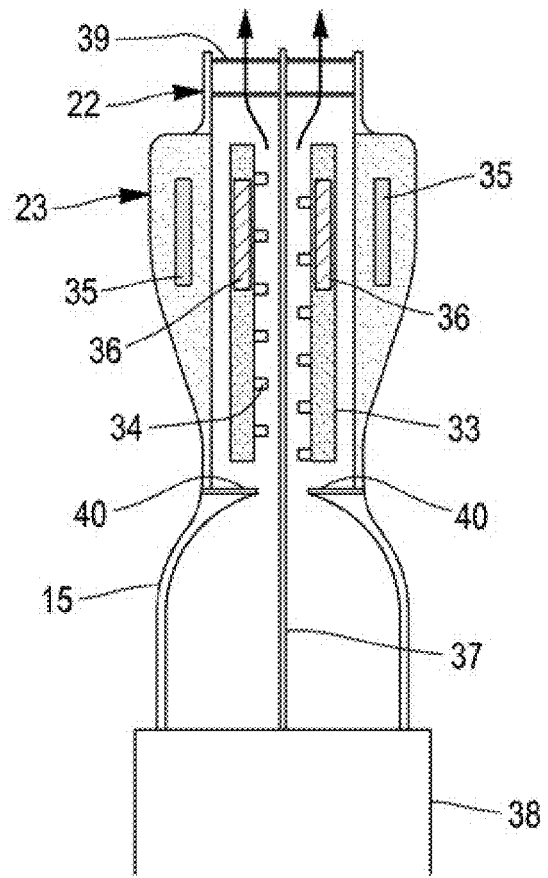
FIG. 5 is a simplified diagrammatic view illustrating the prolongations of the pillars forming inductor vanes and an impeller having internal helical vanes according to the invention.

FIG. 5 shows, in a cross section view, an impeller with internal helical vanes. The motor of the pump comprises a fixed stator, which is the upper body 23, and a rotor or impeller 33. In the example in FIG. 5, the impeller 33 is a hollow right cylinder. The hollow part also has the shape of a right cylinder, but it can have any other shape such as a flared, oblong or structured shape. The hollow central part of the impeller 33 bears on its inner surface a helical vane 34 to propel the fluid towards the outlet head 22. It can be a single vane 34 or several vanes, having a fixed or variable pitch, over the entire length of the inner surface of the impeller or over only a portion. The impeller 33 is designed to be in rotation with respect to the upper body 23. Ideally the upper body 23 is a stator comprising magnetic elements such as magnetic windings 35. The latter can cooperate magnetically with magnetic elements such as for example permanent magnets 36 arranged inside or on the outer surface of the impeller 33. Electronic means (not shown) are provided to control the windings 35 so as to actuate the impeller 33. The assembly constitutes a motor of the brushless type. The gap between the impeller 33 and the upper body 23 is straight, it is inscribed within a right cylinder, but it can have another, non-straight shape, flared or not.

Optionally, a fixed column 37 is arranged inside the impeller 33 and makes it possible to improve the flow of blood when the pump is in operation, i.e. the impeller 33 in rotation with respect to the upper body 23. This column 37 can be fixed by means of the two ends, for example to a fixed bottom part 38 of the casing and to the outlet head 22 via outlet vanes 39. It is also possible to envisage a column 37 fixed at only one end.

Other modes of arrangement of the column 37 can be envisaged, such as for example a column in rotation but fixed in translation; in this case the column 37 can be fixed to the impeller 33 by means of an arm allowing the column to remain within the axis of rotation of the turbine.

Bearing mechanisms can be provided between the impeller and the upper body 23 to hold the impeller. Other means can be provided to hold the impeller in rotation in the casing without contact. It is possible in particular to envisage a suspension mechanism, by fluid, by magnetism etc. with or without retaining edges.

In FIG. 5, the prolongations 40 of the pillars 15 are also shown. These prolongations constitute inductor vanes inside the propulsion chamber. These prolongations are arranged at the inlet of the propulsion chamber 23, 22 to make the flow of the fluid linear in the direction of the impeller.

Figure 6:
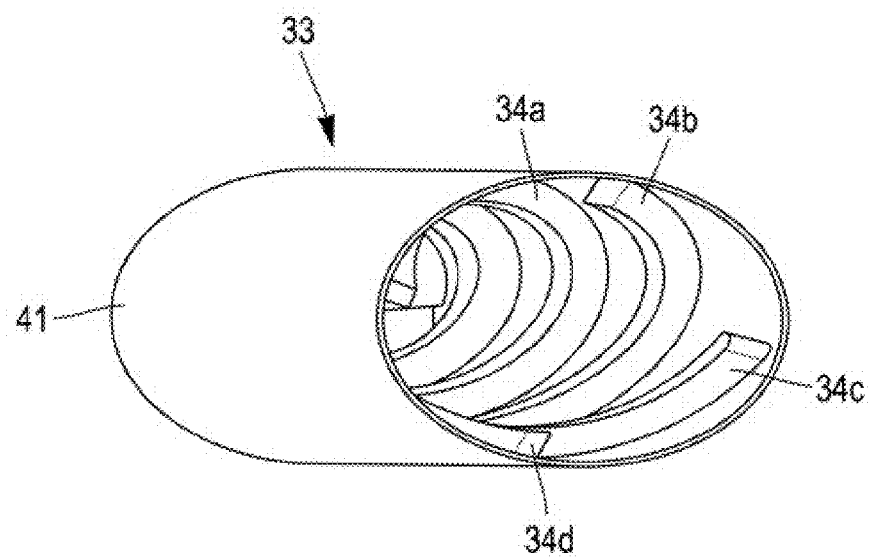
FIG. 6 is a diagrammatic view of an impeller having internal helical vanes according to the invention.

FIG. 6 shows an example of the impeller 33 in FIG. 5. In the example described by way of non-limitative example, it is a body 41 in the shape of a longilinear hollow cylinder the inner wall of which comprises several vanes 34a, 34b, 34c, 34d. Such a turbine can advantageously be used in a pump immersed in a fluid.

The function of the vanes 34a, 34b, 34c, 34d is to make the fluid pass through the impeller. The orientation and the dimensioning of the vanes are intended so that the fluid is drawn then propelled after having passed through the impeller which would be in rotation.

In the example in FIG. 6, the four helical vanes 34a, 34b, 34c, 34d, start from one end of the impeller, are inscribed within helical lines without ever crossing one another, and arrive at the other end.

Of course, the invention is not limited to the examples that have just been described. Numerous adjustments can be made to these examples without exceeding the scope of the present invention as described.

The invention claimed is:

1. A heart pump intended to be positioned partially or entirely in a ventricle of a heart and to generate an induced flow of fluid in the direction of the sigmoid valves of the aorta; said pump comprising:
   a fixed casing provided with a top part, when the heart pump is positioned vertically, forming a propulsion chamber for propelling the fluid towards the top end, and a bottom part attached in a fixed manner to the top part;
   at least one side opening between the top part and the bottom part and forming a chamber for fluid inlet from the outside towards the propulsion chamber;
   a power unit arranged inside the casing to drive the fluid from the side opening right up to the outlet of the propulsion chamber;
the propulsion chamber comprises an upper body and an outlet head; the outlet head having a narrowed external cross section with respect to an external cross section of the upper body, the upper body finishing with a shoulder that reduces a diameter of said upper body to connect with the outlet head; the outlet head having an external cross section the diameter, or the largest distance, of which is comprised between 14 and 16 mm; and in that the propulsion chamber is attached in a fixed manner to the bottom part of the casing by means of linking elements the top part of which is directly connected to the bottom end of the propulsion chamber, the outer surface of the propulsion chamber being flush with the linking elements at the place of connection.

2. The heart pump according to claim 1, characterized in that the external cross section of the upper body has a diameter, or a largest distance, comprised between 17 and 20 mm.

3. The heart pump according to claim 1, characterized in that the external cross section of the upper body has a diameter, or a largest distance, equal to 18 mm.

4. The heart pump according to claim 1, characterized in that the outlet head has a distance along a propulsion axis comprised between 5 and 10 mm.

5. The heart pump according to claim 1, characterized in that it comprises a shoulder at the connection between the upper body and the outlet head, this shoulder having a concave shape.

6. The heart pump according to claim 1, characterized in that the propulsion chamber is in the shape of a straight circular cylinder.

7. The heart pump according to claim 1, characterized in that the upper body has an outer shape that is flared from the inlet chamber right up to the outlet head.

8. The heart pump according to claim 1, characterized in that the linking elements have a general shape that is curved toward the outside.

9. The heart pump according to claim 8, characterized in that the pillars include prolongations right up to the inside of the propulsion chamber; these prolongations serving as inducer vanes to make the flow of the fluid linear in the direction of the top part of the casing.

10. The heart pump according to claim 1, characterized in that the linking elements comprise four pillars.

11. The heart pump according to claim 10, characterized in that the pillars are attached to one another by a lateral band arranged at a distance from the ends.

12. The heart pump according to claim 1, characterized in that the propulsion chamber comprises a rotor to propel the fluid towards the outlet head.

13. The heart pump according to claim 12, characterized in that it comprises a processing unit configured to control the rotor according to a pulsed mode.

* * * * *